United States Patent [19]

Haines

[11] 4,288,455

[45] Sep. 8, 1981

[54] METHOD OF CONTROLLING MOLLUSC PEST

[75] Inventor: Robert G. Haines, Orange Park, Fla.

[73] Assignee: Union Carbide Corporation, New York, N.Y.

[21] Appl. No.: 877,974

[22] Filed: Feb. 15, 1978

[51] Int. Cl.³ .................... A01N 33/24; A01N 37/00; A01N 43/24; A01N 47/10

[52] U.S. Cl. .................................. 424/327; 424/246; 424/270; 424/276; 424/277; 424/298; 424/300

[58] Field of Search ....................... 424/300, 298, 327

[56] References Cited

U.S. PATENT DOCUMENTS 3,920,830 11/1975 Brown et al. ...................... 424/300
4,004,031 1/1977 Drabek ........................ 424/300 X

*Primary Examiner*—Allen J. Robinson
*Attorney, Agent, or Firm*—Clement J. Vicari

[57] ABSTRACT

A method of controlling mollusc by subjecting them to a molluscicidally effective amount of an N-substituted bis-carbamoyl sulfide compound.

10 Claims, No Drawings

METHOD OF CONTROLLING MOLLUSC PEST

This invention relates to a method of controlling molluscs by subjecting them to a molluscidally effective amount of a N-substituted bis-carbamoyl sulfide compound. More particularly, this invention relates to a method of controlling molluscs which comprises subjecting them to a molluscidally effective amount of a compound of the formula:

wherein:

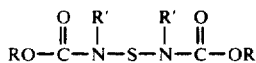

R is:

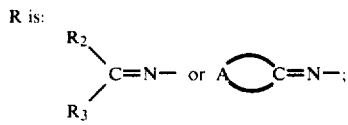

wherein:

$R_2$ is alkyl, alkylthio, alkylsulfinyl, alkylsulfonyl alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy or $R_4R_5$—NCO— groups; or $R_2$ is phenyl, $R_4R_5NCO$— or $R_6CON(R_4)$—; wherein:

$R_4$ and $R_5$ are individually hydrogen or alkyl;

$R_6$ is hydrogen, alkyl or alkoxy;

$R_3$ is hydrogen, alkyl, alkylthio, alkylsulfenyl alkylsulfonyl or cyano;

A is a four or five member divalent aliphatic chain which includes one or two divalent oxygen, sulfur, sulfinyl or sulfonyl groups and which may include not more than one divalent amino, alkylamino or carbonyl groups, in any combination;

provided that the total number of carbon atoms in R may not exceed eight and provided further that when $R_2$ is alkyl substituted with alkylthio, $R_3$ is cyano alkyl or alkylthio; and R' is alkyl containing from one to four carbon atoms.

The following compounds are illustrative of useful compounds:

N,N'-bis-[1-Ethylthioacetaldehyde O-(N-methylcarbamoyl)oxime]sulfide.

N,N'-bis-[1-Isopropylthioacetaldehyde O-(N-methylcarbamoyl)oxime]sulfide.

N,N'-bis-[1-(2-cyanoethylthio)acetaldehyde O-(N-methylcarbamoyloxime]sulfide.

N,N'-bis-[5-Methyl-4-(O-(N-methylcarbamoyl)oximino)-1,3-oxathiolane]sulfide.

N,N'-bis-[2-(O-(N-methylcarbamoyl)oximino)-1,4-dithiane]sulfide.

N,N'-bis-[4-(O-(N-methylcarbamoyl)oximino)-1,3-dithiolane]sulfide.

N,N'-bis-[5,5-dimethyl-4-(O-(N-methylcarbamoyl)oximino)-1,3-dithiolane]sulfide.

N,N'-bis-[3,5,5-trimethyl-2-(O-N-methylcarbamoyl)oximino)thiazolidin-4-one]sulfide.

N,N'-bis-[4,5,5-trimethyl-2-(O-(N-methylcarbamoyl)oximino)thiazolidin-3-one]sulfide.

N,N'-bis-[2-(O-(N-methylcarbamoyl)oximino)-1,3-dithiolane]sulfide

N,N'-bis-[2-cyano-2-methylpropionaldehyde O-(N-methylcarbamoyl)oximino]sulfide

N,N'-bis-[2-nitro-2-methylpropionaldehyde O-(N-methylcarbamoyl)oxime]sulfide.

N,N'-bis-[1-Methylthio-N'',N''-dimethylcarbamoylformaldehyde O-(N-methylcarbamoyl)oxime]sulfide.

N,N'-bis-[4-Methyl-2-(O-(N-methylcarbamoyl)oximino)-tetrahydro-1,4-thiazin-3-one]sulfide N,N'-bis-[3,3-Dimethyl-1-methylthiobutanone-2,O-(N-methylcarbamoyl)oxime]sulfide.

N,N'-bis-[3-Methylthiobutanone-2 O-(N-methylcarbamoyl)oxime]sulfide

N,N'-bis-[3-Methylsulfonylbutanone-2 O-(N-methylcarbamoyl)oxime]sulfide.

N,N'-bis-[2-Methylsulfonyl-2-methylpropionaldehyde O-(N-methylcarbamoyl)oxime]sulfide.

N,N'-bis-[1-Methylthiopyruvaldehyde O-(N-methylcarbamoyl)oxime]sulfide.

N,N'-bis-[3,3-Dimethyl-1-methylsulfonylbutanone-2 O-(N-methylcarbamoyl)oxime]sulfide.

N,N'-bis-1-[N-(Dimethylaminomethylene)carbamoyl]-1-methylthioformaldehyde O-(N-methylcarbamoyl)oxime]sulfide.

N,N'-bis-[1-Methylthio-1-ethoxycarbonylformaldehyde O-(N-methylcarbamoyl)oxime]sulfide N,N'-bis-[1,3,5-Oxadithiane-4 O-(N-methylcarbamoyloximino)]sulfide N,N'-bis-[1,3,5-Trithiane-2 O-(N-methylcarbamoyloximino)]sulfide N,N'-bis-3-[O-(N-methylcarbamoyl)oximino-1,4-oxathiane]sulfide N,N'-bis-[1-cyano-2,2-dimethylpropionaldehyde O-(N-methylcarbamoyloxime)]sulfide.

N,N'-bis-[4-methyl-2-(O-(N-methylcarbamoyl)oximino-tetrahydro-1,4-thiazin-5-one]sulfide.

The compounds that are useful in the conduct of the method of this invention exhibit outstanding molluscicidally activity. These compounds are also characterized by substantially reduced mammalian toxicity and phytotoxicity in comparison with known molluscicidally active compounds.

Preferred for use in the method of this invention are compounds in which

R' is methyl;

R is 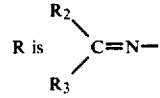

$R_2$ is alkyl, alkylthio, cyanoalkyl, nitroalkyl or alkylthioalkyl;

$R_3$ is alkyl or alkylthio.

The compounds useful in the conduct of the method of this invention can be prepared by the methods described in U.S. patent Ser. No. 636,373, entitled SYMMETRICAL BIS-CARBAMATE COMPOUNDS, filed Dec. 1, 1975.

The symmetrical bis-carbamoyl sulfides utilized as the active toxicant in the method of this invention can be prepared conveniently by the method shown in the following general reaction scheme:

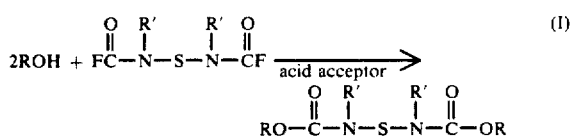

wherein R and R' are as defined above.

Two equivalents of the oxime reactant (ROH) are reacted with the bis-carbamoyl fluoride in the presence of two equivalents of an acid acceptor, preferably in an inert solvent such as toluene, benzene, methylene, chloride, xylene and the like. The acid acceptor employed can be either an organic or inorganic base such as triethylamine or sodium or potassium hydroxide. A phase transfer agent such as a crown ether may also be employed. Any conventional inert solvent can be used, such as benzene, toluene, dioxane, tetrahydrofuran, ethylether, methylene chloride or the like.

This reaction may also be carried out in a two phase system using an aqueous solution of an inorganic base as one phase and an organic solvent including a quaternary ammonium salt as a phase transfer agent as the second phase. The reaction temperature is not critical. The reaction goes essentially to completion at room temperature. Elevated temperatures may be employed if it is desired to reduce reaction time.

An alternative method of preparing the symmetrical bis-carbamoyl sulfide compounds utilized in the process of this invention is illustrated by the following general reaction system:

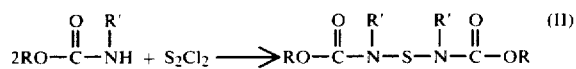

(II)

In this procedure two equivalents of a carbamate compound are reacted with sulfur monochloride in the presence of two equivalents of an acid acceptor such as pyridine, preferably in an inert solvent to produce the symmetrical bis-carbamoyl sulfides of this invention. The carbamate compounds employed in this procedure are known compounds which are generally prepared by reacting the corresponding oxime compounds with an alkylisocyanate compound.

The oxime reactants (ROH) employed in the reactions described above are known compounds which can be prepared by conventional methods. See for example, U.S. Pat. Nos. 3,752,841, 3,726,908, 3,843,669, and Belgian Pat. Nos. 813,206 and 815,513.

The active compounds useful in the method of this invention may be applied as molluscicides according to methods known to those skilled in the art. Molluscicidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifing agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre. The active toxicant can be applied either to the plant or to the soil around the plant.

The molluscicides contemplated herein prevent attack by mollusc upon plants or other material to which the molluscidally active compounds are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. Mixtures of the active compound of this invention may be employed as well as combinations of the active compounds of this invention with other biologically active compounds, such as, insecticides, miticides, fungicides and herbicides. They may also be formulated with fertilizer and with plant growth regulators.

The following examples are presented to more particularly illustrate the invention.

EXAMPLE 1

Preparation of Bis-(N-Methyl-N-fluorocarbonyl)amino sulfide

To a polypropylene reactor containing 80 g (4.0 m) of hydrogen fluoride in 1800 ml of toluene, cooled to −40° C. was added dropwise with stirring 228 g (4.0 m) of methylisocyanate, over a period of 20 min. The reaction mixture was allowed to warm to 0° C. and was maintained at this temperature for 1 hour. Then 60 g (2 m) of freshly distilled sulfur dichloride was added followed by a slow addition (4.4 m) of pyridine at −20° to 0° C. After stirring for 2 hrs. at −10° C. and for 16 hrs. at ambient temperature, the reaction mixture was diluted with 500 ml of water. The toluene layer was further washed with 3×500 ml water dried and distilled to yield 244 g (66 percent) of the product. B.P. 55°–57° C./0.25 mm. m.p. 40°–41° C.

Calc'd for $C_4H_6F_2N_2O_2S$: C, 26.09; H, 3.28; N, 15.21; Found: C, 26.19; H, 3.20; N, 14.79.

EXAMPLE II

Preparation of N,N'-bis-[1-Methylthioacetaldehyde O-(N-methylcarbamoyl)oximino]sulfide (Method I)

Procedure A

To a solution of 0.50 g of bis-(N-methyl-N-fluorocarbonyl)amino sulfide and 0.526 g of 1-methylthioacetaldoxime in 15 ml dioxane was added 0.505 g of triethylamine. After stirring for 20 hrs. at room temperature, the reaction mixture was diluted with water. The N,N'-bis[1-methylthioacetaldehyde O-(N-methylcarbamoyl)oximino]sulfide solid was filtered and taken in methylene chloride. The organic extract was washed with water, dried and concentrated. Weight of product 0.60 g. m.p. 173°-174° C.

Calc'd. for $C_{10}H_{18}N_4O_4S_3$: C, 33.88; H, 5.12; N, 15.81; Found: C, 33.72; H, 5.15; N, 15.49

EXAMPLE III

Preparation of N,N'-bis-[1-Methylthioacetaldehyde O-(N-methylcarbamoyl)oximino]sulfide (Method I)

Procedure B

To a solution of 36.9 g of bis-(N-methyl-N-fluorocarbonyl)amino sulfide and 42.0 g of 1-methylthioacetaldoxime in 500 ml of toluene was added 40.47 g of triethylamine. The spontaneous exotherm raised the temperature to 32° C. After stirring for 16 hrs. at ambient temperature an additional 100 ml of toluene was added and the reaction mixture heated to about 45° C. for 2 hrs. It was then cooled to 10° C. and filtered. The solid was washed with water and rinsed with isopropanol and air dried to yield 54.46 g of white solid N,N'-bis[1-methylthioacetaldehyde O-(N-methylcarbamoyl)oximino]sulfide m.p. 170°-173° C., recrystallized from methylene chloride m.p. 173°-174° C.

EXAMPLE IV

Preparation of N,N'-bis-[1-Methylthioacetaldehyde O-(N-methylcarbamoyl)oximino]sulfide (Method II)

To a solution of 1.62 g of 1-methylthioacetaldehyde O-(N-methylcarbamoyl)oxime and 0.67 g of sulfur monochloride in 25 ml of toluene was added 0.79 g of pyridine. After stirring for 16 hrs. the solid was filtered off, was washed with water and dried to yield 0.7 g of the N,N'-bis-[1-methylthioacetaldehyde O-(n-methylcarbamoyl)oximino]sulfide m.p. 174°-178° C. (identical by tlc and nmr to the product obtained in Examples II and III).

EXAMPLE V

Preparation of N,N'-bis-[1-(2-cyanoethylthio)acetaldehyde O-(N-methylcarbamoyl)oximino]sulfide To a suspension of 14.4 g of 1-(2-cyanoethylthio) acetaldoxime and 8.63 g of bis-(N-methyl-N-fluorocarbonyl) amino sulfide in 70 ml of toluene was added dropwise 10.1 g of triethylamine diluted with 10 ml of toluene. The temperature of the reaction was maintained under 30° C. After stirring for 20 hrs. at room temperature the solid suspension was filtered and washed with 10 percent isopropanol in water. The filtrate was discarded and the solid N,N'-bis-[1-(2-cyanoethylthio)acetaldehyde O-(N-methylcarbamoyl)oximino]sulfide (10.0 g) was crystallized from acetonitrile-methylene chloride. m.p. 189°-190° C.

Calc'd for $C_{14}H_{20}N_6O_4S_3$: C, 38.87; H, 4.66; N, 19.43. Found: C, 38.50; H, 4.61; N, 19.11.

EXAMPLE VI

Preparation of N,N'-bis-[2-Methylsulfonyl-2-methylpropionaldehyde O-(N-methylcarbamoyl)oximino]sulfide To a solution of 4.0 g of 2-methylsulfonyl-2-methylpropionaldoxime and 2.1 g of bis-(N-methyl-N-fluorocarbonyl) aminosulfide in 50 ml of toluene was added 2.45 g of triethylamine diluted with 25 ml of toluene. The reaction mixture was allowed to stand at ambient temperature for 62 hours. The precipitated solid was removed by filtration, was dissolved in methylene chloride, washed with water and dried over magnesium sulfate. On concentration and recrystallization from ethyl acetate it yielded 2.9 g of N,N'-bis-[2-methylsulfonyl-2-methylpropionaldehyde O-(N-methylcarbamoyl)oximino]sulfide in the form of a white solid. m.p. 124°-125° C.

Calc'd for $C_{14}H_{26}N_4O_8S_3$: C, 35.43; H, 5.52; N, 11.81; Found: C, 35.38; H, 5.56; N, 11.57.

EXAMPLE VII

Preparation of N,N'-bis-[2-Cyano-2-methylpropionaldehyde O-(M-methylcarbamoyl)oximino]sulfide To a solution of 4.48 g of 2-cyano-2-methylpropional doxime and 3.37 g of bis-(N-methyl-N-fluorocarbonyl) amino sulfide in 75 ml of toluene was added 4.04 g of triethylamine diluted with 25 ml of toluene. After stirring for 2 hrs. an additional 0.63 g of bis-(N-methyl-N-fluorocarbonyl)amino sulfide was added and the reaction mixture heated at 30°-40° C. for 2.5 hrs. The solvent was removed under reduced pressure and the residue was dissolved in ethylacetate and water. The organic layer was washed with water, dried over magnesium sulfate and concentrated under reduced pressure. The product, N,N'-bis-[2-cyano-2-methylpropionaldehyde O-(N-methylcarbamoyl)oximino]sulfide was crystallized from isopropylether-ethyl acetate. Weight of product 1.32 g m.p. 110°-112° C.

Calc'd for $C_{14}H_{20}N_6O_4S$: C, 45.64; H, 5.46; N, 22.81; Found: C, 45.49; H, 5.49; N, 22.44.

EXAMPLE VIII

Preparation of N,N'-bis-[1-Methylthio-1-(N'',N''-dimethylcarbamoyl)-formaldehyde O-(N-methylcarbamoyl)oximino]sulfide To a solution of 3.24 g of 1-methylthio-N,N-dimethylcarbamoyl formaldoxime and 2.0 g of bis-(N-methyl-N-fluorocarbonyl)amino sulfide in 100 ml of toluene was added 2.02 g of triethylamine. After stirring for 20 hrs. the reaction mixture was washed with water. The toluene solution was dried over magnesium sulfate and concentrated to yield a solid residue. Crystallization from ethylacetate yielded 2.1 g of white solid N,N'-bis-[1-methylthio-1-(N'',N''-dimethylcarbamoyl)formaldehyde O-(N-methylcarbamoyl)oximino]sulfide. m.p. 190°-192° C.

Calc'd for $C_{14}H_{24}N_6O_6S_3$: C, 35.88; H, 5.16; N, 17.9; Found: C, 35.75; H, 5.56; N, 17.5.

EXAMPLE IX

Preparation of N,N-bis-[1,4-Dithiane-2-O-(N-methylcarbamoyl)oximino]sulfide

Prepared by the procedure employed in Example VIII by reacting 5.0 of 2-oximino-1,4-dithiane with 2.89 g of bis-(N-methyl-N-fluorocarbonyl)amino sulfide and 3.39 g of triethylamine. Weight of the product N,N'-bis-[1,4-dithiane-2-O-(N-methylcarbamoyl)oximino]sulfide 4.7 g m.p. 209°-211° C.

Calc'd for $C_{12}H_{18}N_4O_4S_5$: C, 32.56; H, 4.10; N, 12.66; Found: C, 32.10; H, 3.87; N, 12.21.

EXAMPLE X

The compound of Example II was evaluated to determine its molluscicidal activity against a variety of mollusc. The compound was evaluated in a formulation which was prepared as follows.

A solution of the test compound was prepared by dissolving the compound in acetone to the desired weight percent employed in the test described hereinbelow. Milbrun wheat bran was used as the carrier attractant of the bait. The bait was prepared by immersing the wheat bran in the acetone/test compound solution. The wheat bran was removed from the test solution and the residual acetone allowed to evaporate.

Laboratory reared brown garden snails (*Heli aspersa*); European Red-slug (*arion ater rufus*); and European black slug (*arion ater*) were used as the test species. Temperatures in the molluscitorium testing laboratory were maintained from about 64° to about 70° F. during the testing.

The testing boxes contained a layer of moist soil with an open arena of about ninety square feet, the open area was connected to a covered "refuge." Five individual members of each test species were confined in each box with the salt barrier for approximately forty-eight hours prior to the initiation of the test. During this period the test species were not given food of any kind. After evaporating the acetone a teaspoon of the bait was placed in the center of each testing box arena where the bait was readily available to the mollusc as they emerged from the refuge at night in search of food. Observations were made at regular intervals for the purpose of determining the number of mollusc lying in the arenas, or dead. The criterion of death was lack of any sign of contraction when a mollusc was tapped sharply with a probe. Each experiment was conducted in three replicates. In Table I below is set forth mollusc toxicity data. The data is expressed in percent mortality, i.e. the percent of mollusc dead after ten days of exposure to the test compound.

The test results set forth in Table I clearly illustrate the high level of molluscicidal activity exhibited by the compounds utilized as the active toxicant in the method of this invention. It should be understood that the mollusc tested are representative of a wider variety of mollusc that can be controlled by the method of this invention.

TABLE I

| Compound | Weight % Compound in Bait | PERCENT MORTALITY AFTER TEN DAYS OF EXPOSURE | | |
|---|---|---|---|---|
| | | European Black Slug | European Reg Slug | Brown Garden Snail |
| N,N'-bis-[1-Methylthioacetaldehyde-O-(N-methyl-carbamoyl)oximino]sulfide | 2 | 66.7 | 33.3 | 73.3 |
| | 4 | 100 | 46.7 | 93.3 |

What is claimed:

1. A method of controlling mollusc which comprises subjecting them to a molluscicidally effective amount of a compound of the formula:

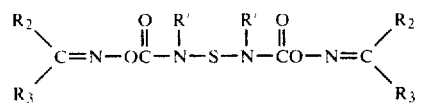

wherein:
R' is alkyl having from 1 to 4 carbon atoms;
$R_2$ is alkyl, alkylthio, alkylsulfinyl, alkylsulfonyl, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy or phenyl; or $R_2$ is $R_4 R_5$—NCO or $R_6 CON(R_4)$— groups, wherein:
$R_4$ and $R_5$ are individually hydrogen or alkyl;
$R_6$ is hydrogen, alkyl or alkoxy;
$R_3$ is hydrogen, alkyl, alkylthio, alkylsulfinyl, alkylsulfonyl or cyano;
with the provisos that:
A. the total number of carbon atoms in $R_2$ and $R_3$ together may not exceed eight; and
B. when $R_2$ is alkyl substituted with alkylthio, $R_3$ is cyano, alkyl, and alkylthio.

2. A method according to claim 1 wherein R' is methyl.

3. A method according to claim 1 wherein $R_3$ is alkyl.

4. A method according to claim 1 wherein $R_2$ is alkylthio.

5. A method according to claim 1 wherein said compound is N,N'-bis-[1-methylthioacetaldehyde O-(N-methylcarbamoyl)oximino]sulfide.

6. A method according to claim 1 wherein said compound is N,N'-bis-[1-(2-cyanoethylthio)acetaldehyde O-(N-methylcarbamoyl)oximino]sulfide.

7. A method according to claim 1 wherein said compound is N,N'-bis-[1-Isopropylthioacetaldehyde O-(N-methylcarbamoyl)oxime]sulfide.

8. A method according to claim 1 wherein said compound is N,N'-bis-[2-Methylsulfonyl-2-methylpropionaldehyde O-(N-methylcarbamoyl)oxime]sulfide.

9. A method according to claim 1 wherein $R_2$ is alkylthio, alkylsulfinyl or alkylsulfonyl.

10. A method according to claim 1 wherein:
R' is methyl;
$R_2$ is alkylthio, alkylsulfinyl or alkylsulfonyl;
$R_3$ is alkyl.

* * * * *